United States Patent [19]

Vora et al.

[11] 4,381,417
[45] Apr. 26, 1983

[54] CATALYTIC DEHYDROGENATION PROCESS

[75] Inventors: Bipin V. Vora, Elk Grove Village; Dennis E. O'Brien; Norman H. Scott, both of Arlington Heights, all of Ill.

[73] Assignee: UOP Inc., Des Plaines, Ill.

[21] Appl. No.: 327,655

[22] Filed: Dec. 4, 1981

[51] Int. Cl.³ .............................................. C07C 5/36
[52] U.S. Cl. .................................... 585/655; 585/654; 62/23; 62/24; 62/27
[58] Field of Search .................... 62/11, 23, 24, 27, 28; 585/654, 655

[56] References Cited

U.S. PATENT DOCUMENTS

| | | | |
|---|---|---|---|
| 2,620,314 | 12/1952 | Hoekstra | 252/448 |
| 3,119,677 | 1/1961 | Moon et al. | 62/28 |
| 3,647,680 | 3/1972 | Greenwood et al. | 208/65 |
| 4,257,794 | 3/1981 | Shirokov et al. | 62/23 |
| 4,272,270 | 6/1981 | Higgins | 62/24 |
| 4,343,633 | 8/1982 | Kick et al. | 62/23 |

FOREIGN PATENT DOCUMENTS

| | | | |
|---|---|---|---|
| 1041003 | 6/1978 | Canada | 62/24 |
| 3028565 | 8/1976 | Japan | 62/11 |

OTHER PUBLICATIONS

Berg et al., Oil and Gas Journal, Nov. 10, 1980, pp. 191-197.

Primary Examiner—Delbert E. Gantz
Assistant Examiner—A. Pal
Attorney, Agent, or Firm—James R. Hoatson, Jr.; Robert W. Welch; William H. Page, II

[57] ABSTRACT

A process for the catalytic dehydrogenation of low molecular weight paraffinic hydrocarbons is disclosed. The process is particularly directed to the separation of hydrogen from the olefinic hydrocarbon products and unreacted paraffinic hydrocarbons.

8 Claims, 1 Drawing Figure

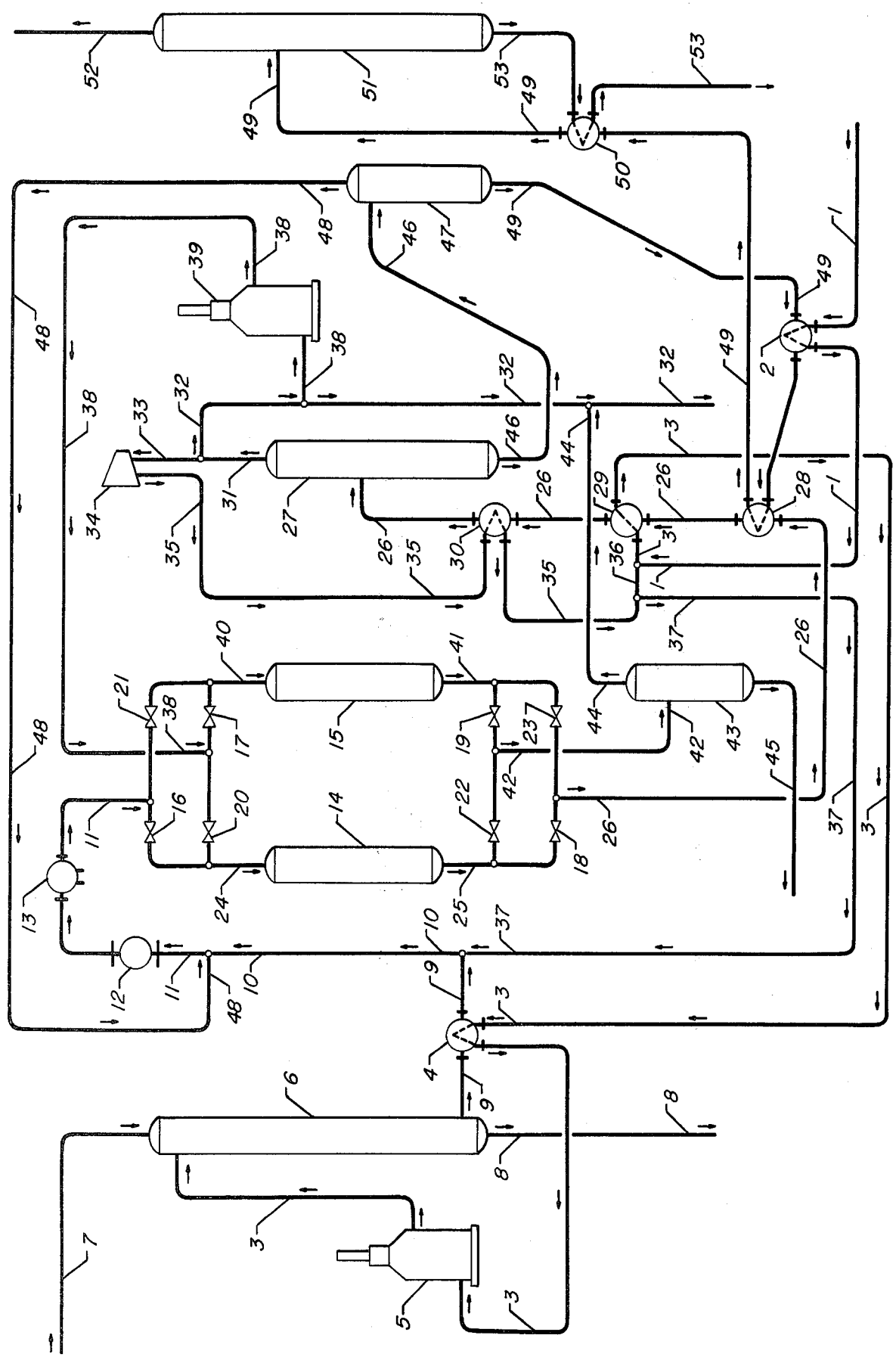

CATALYTIC DEHYDROGENATION PROCESS

This invention relates to a process for the catalytic dehydrogenation of $C_2+$, normally gaseous, paraffinic hydrocarbons to produce low molecular weight, normally gaseous, monoolefinic hydrocarbons. The catalytic dehydrogenation of low molecular weight, normally gaseous, paraffinic hydrocarbons is an established and well known hydrocarbon conversion process in the petroleum refining industry. The monoolefinic hydrocarbon products are generally useful as intermediates in the production of other more valuable hydrocarbon conversion products, and the catalytic dehydrogenation process is typically utilized in conjunction with various other hydrocarbon conversion processes to yield a desired final product. For example, utilizing liquid petroleum gas (LPG)—a compressed or liquefied gas consisting of propane and butane or mixed butanes derived as a by-product of petroleum refining—as a starting material, catalytic dehydrogenation can be utilized to produce propylene and/or butylenes in conjunction with an HF alkylation unit wherein said olefins are alkylated with isobutane to produce a high octane motor fuel; or in conjunction with a catalytic condensation unit wherein said olefins are condensed to form tetramers or polymer gasoline; or in conjunction with an etherification unit wherein isobutylene is reacted with methanol to produce methyl-t-butylether, a highly desirable gasoline additive.

Notwithstanding that certain of the catalyzed hydrocarbon conversion processes, including the dehydrogenation process herein contemplated, involve hydrogen-producing reactions, it has been the practice to charge hydrogen to the reaction zone in admixture with the hydrocarbon charge stock. This practice has been found to promote catalyst stability. The hydrogen admixed with the hydrocarbon charge stock is almost invariably recycle hydrogen separated as a hydrogen-rich vapor phase from the reaction zone effluent. Hydrogen in excess of that required for recycle purposes is recovered as net hydrogen and may be utilized in other processes integrated into the overall petroleum refining operation, used as fuel, or exported as a refinery product.

The separation and recycle of a hydrogen-rich vapor phase from a reaction zone effluent is a common practice. In those hydrocarbon conversion processes wherein the reaction zone effluent consists largely of normally liquid hydrocarbons and hydrogen, the separation of a hydrogen-rich vapor phase is a relatively simple matter. This is generally accomplished by cooling the reaction zone effluent and condensing out the normally liquid hydrocarbons in a gas-liquid separator. The further purification of the hydrogen-rich vapor phase can be accomplished, if so desired, at more severe conditions of temperature and pressure, but said purification will involve the treatment of substantially less than the total reaction zone effluent. In contrast, when the reaction zone effluent consists largely of normally gaseous hydrocarbons and hydrogen, as is the case with the catalytic dehydrogenation process herein contemplated, the separation of a vapor phase suitably rich in hydrogen requires treatment of the total reaction zone effluent at the more severe conditions of temperature and pressure and entails a substantial increase in utilities demand.

In the latter case, the problem is further compounded with respect to the dehydrogenation of $C_3$–$C_4$ paraffinic hydrocarbons to produce the corresponding monoolefins. Equilibrium conditions relating to the dehydrogenation reaction limit conversions to from about 30 to about 50 mol.% at optimum conditions of temperature and pressure. It follows that the overall conversion will be reduced in proportion to the amount of olefinic product returned to the dehydrogenation zone in admixture with the recycle hydrogen. It is therefore imperative that in the separation of the normally gaseous hydrocarbons from the recycle hydrogen, substantially all of the olefinic product must be separated to assure an optimum conversion.

It is an object of this invention to present an improved process for the catalytic dehydrogenation of normally gaseous paraffinic hydrocarbons. It is a more specific object of this invention to provide an improved process for the separation of a hydrogen-rich vapor phase from a reaction zone effluent resulting from the catalytic dehydrogenation of normally gaseous paraffinic hydrocarbons.

In one of its broad aspects, the present invention embodies a catalytic dehydrogenation process which comprises the steps of (a) charging a $C_2$–$C_6$ paraffinic hydrocarbon into a reaction zone in admixture with hydrogen and contacting said mixture therein with a dehydrogenation catalyst at dehydrogenation conditions of temperature and pressure effecting the formation of a reaction zone effluent stream comprising hydrogen, an olefinic hydrocarbon product, and unreacted paraffinic hydrocarbon; (b) compressing and cooling said effluent stream to a pressure and temperature effecting the formation of a liquid phase comprising said hydrocarbons and a hydrogen-rich vapor phase, and introducing said effluent stream into a gas-liquid separation zone maintained at said conditions of temperature and pressure; (c) recovering said hydrocarbon phase; (d) recovering one portion of said vapor phase substantially equivalent to the net hyrogen make; (e) expanding the remaining portion of said vapor phase and effecting a substantial reduction in the pressure and temperature thereof; (f) passing the thus cooled vapor phase in indirect heat exchange relationship with the effluent stream of step (b) to promote said temperature conditions in said gas-liquid separation zone; (g) thereafter combining one portion of the vapor phase with the effluent stream from step (a) whereby said vapor phase is recycled to said gas-liquid separation zone to control the amount of vapor expanded in accordance with step (c) and the temperature of said separation zone in accordance with step (f); and, (h) recycling the remaining portion of the hydrogen-rich vapor phase to said reaction zone in admixture with the paraffinic hydrocarbon charged thereto in accordance with step (a).

Another embodiment relates to a catalytic dehydrogenation process which comprises the steps of (a) charging a $C_2$–$C_6$ paraffinic hydrocarbon into a reaction zone in admixture with hydrogen and contacting said mixture therein with a dehydrogenation catalyst at dehydrogenation conditions including a temperature of from about 900° to about 1400° F. and a pressure of from about 0 to about 35 psig, and effecting the formation of a reaction zone effluent stream comprising hydrogen, an olefinic hydrocarbon product and unreacted paraffinic hydrocarbon; (b) compressing and cooling said effluent stream to a pressure of from about 100 to about 400 psig and a temperature of from about −30° to about −120° F. and forming a liquid phase comprising said olefinic and paraffinic hydrocarbons and a hydrogen-rich vapor phase, and introducing said effluent stream into a gas-liquid separation zone maintained at said conditions of pressure and temperature; (c) recovering said liquid hydrocarbon phase; (d) recovering one portion of said vapor phase substantially equivalent to the net hydrogen make; (e) expanding the remaining portion of said vapor phase and effecting a reduction in pressure to from about 15 to about 75 psig, and in temperature to from about −115° to about −200° F; (f) passing the thus cooled vapor phase in indirect heat exchange relationship with the effluent stream of step (b) to promote said temperature conditions in said gas-liquid separation zone; (g) thereafter combining one portion of the vapor phase with the effluent stream from step (a) whereby said vapor phase is recycled to said gas-liquid separation zone to control the amount of vapor expanded in accordance with step (c) and the temperature of said separation zone in accordance with step (f); and, (h) recycling the remaining portion of the hydrogen-rich vapor phase to said reaction zone in admixture with the paraffinic hydrocarbon charged thereto in accordance with step (a).

One of the more specific embodiments relates to a catalytic dehydrogenation process which comprises the steps of (a) charging isobutane into a reaction zone in admixture with hydrogen and contacting said mixture therein with a dehydrogenation catalyst at dehydrogenation conditions including a temperature of from about 1000° to about 1300° F. and a pressure of from about 0 to about 20 psig, and effecting the formation of a reaction zone effluent stream comprising hydrogen, isobutylene and isobutane; (b) compressing and cooling said effluent stream to a pressure of from about 150 to about 250 psig and a temperature of from about −30° to about −70° F. and forming a liquid hydrocarbon phase comprising said isobutylene and isobutane, and a hydrogen-rich vapor phase, and introducing said effluent stream into a gas-liquid separation zone maintained at said conditions of pressure and temperature; (c) recovering said liquid hydrocarbon phase; (d) recovering one portion of said vapor phase substantially equivalent to the net hydrogen make; (e) expanding the remaining portion of said vapor phase and effecting a reduction in pressure to from about 40 to about 60 psig, and in temperature to from about −120° to about −130° F; (f) passing the thus cooled vapor phase in indirect heat exchange relationship with the effluent stream of step (b) to promote said temperature conditions in said gas-liquid separation zone; (g) thereafter combining one portion of the vapor phase with the effluent stream from step (a) whereby said vapor phase is recycled to said gas-liquid separation zone to control the amount of vapor expanded in accordance with step (c) and the temperature of said separation zone in accordance with step (f); and, (h) recycling the remaining portion of the hydrogen-rich vapor phase to said reaction zone in admixture with the paraffinic hydrocarbon charged thereto in accordance with step (a).

The catalytic dehydrogenation process herein contemplated will preferably utilize a catalytic composite comprising a platinum group metal component, a tin component, and an alkali metal component composited with a porous, high surface area, adsorbent support or carrier material. Of the platinum group metals, i.e., platinum, palladium, ruthenium, rhodium, osmium and iridium, platinum is a preferred catalyst component. The platinum component will generally comprise from about 0.01 to about 2.0 wt.% of the catalytic composite, and the tin component will generally comprise from about 0.01 to about 5 wt.% thereof. Of the alkali metals, i.e., cesium, rubidium, potassium, sodium and lithium, lithium and/or potassium are preferred. The alkali metal will generally constitute from about 0.1 to about 3.5 wt.% of the catalytic composite. One preferred catalytic composite comprises from about 0.1 to about 1.0 wt.% platinum, from about 0.1 to about 1.0 wt.% tin and from about 0.4 to about 3.0 wt.% lithium or potassium composited with a porous absorbent support or carrier material having a surface area of from about 25 to about 500 m$^2$/g.

Suitable high surface area adsorbent materials for use as a catalyst support or carrier materials include the various charcoals produced by the destructive distillation of wood, peat, lignite, nutshells, bones and other carbonaceous matter, and preferably such charcoals as have been heat treated, or chemically treated, or both, to form a highly porous particle structure of increased adsorbent capacity, and generally defined as activated carbon. Said adsorbent materials also include the naturally occurring clays and silicates, for example, diatomaceous earth, fuller's earth, kieselguhr, attapulgus clay, feldspar, montmorillonite, halloysite, kaolin, and the like, and also the naturally occurring or synthetically prepared refractory inorganic oxides such as alumina, silica, zirconia, etc., or combinations thereof like silica-alumina, silica-zirconia, alumina-zirconia and the like. The preferred carrier materials are the refractory inorganic oxides with best results being obtained with an alumina support or carrier material.

The reaction zone of the present invention preferably comprises at least one radial flow reactor through which the catalytic composite gravitates downwardly to allow a substantially continuous replacement of the catalyst with fresh and/or regenerated catalyst. A detailed description of the moving bed reactors herein contemplated may be obtained by reference to U.S. Pat. No. 3,978,150. With regard to the moving bed type of operation, a particularly preferred form of alumina is the sphere, especially alumina spheres prepared substantially in accordance with the oil-drop method described in U.S. Pat. No. 2,620,314. Briefly, said method comprises dispersing droplets of an alumina sol in a hot oil bath. The droplets are retained in the oil bath until they set into firm gel spheroids. The spheroids are continuously separated from the bath and subjected to specific aging treatments to promote certain desirable properties. The spheres are subsequently dried and calcined to develop pore characteristics and high surface area.

The dehydrogenation reaction is a highly endothermic reaction which is typically effected at near atmospheric pressure conditions. The precise dehydrogenation conditions employed in the dehydrogenation reaction zone will depend on a variety of factors including the composition of the paraffinic hydrocarbon feedstock, the activity of the selected catalyst, and the hydrocarbon conversion rate. In general, dehydrogenation conditions include a pressure of from about 0 to about 35 psig and a temperature of from about 900° to about 1400° F. The paraffinic hydrocarbon feedstock is suitably charged to the reaction zone and contacted with the catalyst contained therein at a liquid hourly space velocity of from about 1 to about 10. Hydrogen, principally recycle hydrogen, is suitably admixed with the hydrocarbon feedstock in a mole ratio of from about 1 to about 10. Preferred dehydrogenation conditions, particularly with respect to $C_3$–$C_4$ paraffinic hydrocarbon feedstocks, include a pressure of from about 0 to about 20 psig and a temperature of from about 1000° to about 1300° F., a liquid hourly space velocity of from about 2 to about 6, and a hydrogen/hydrocarbon mole ratio of from about 1 to about 4.

The further description of the process of this invention is presented with reference to the attached schematic drawing. The drawing represents one preferred embodiment of the invention and is not intended as an undue limitation on the generally broad scope of the invention as set out in the appended claims. Only those compressors, heaters, heat exchangers, coolers and valves are shown that are useful in the description of the process. The utilization of other miscellaneous hardware such as pumps, instrumentation and controls have been omitted as not essential to a clear understanding of the process, the use of such hardware being well within the purview of one skilled in the art.

Referring then to the drawing, a hydrocarbon feed stream comprising isobutane is charged to the dehydrogenation process from a deisobutanizer column which is not shown. The feed stream is introduced by way of line 1 at a temperature of about 100° F. and at a pressure of about 85 psig, and the feed stream is then processed through a heat exchanger 2 to effect an indirect heat exchange with a liquid hydrocarbon stream passing through line 49 at a temperature of about −51° F. and originating as hereinafter described. The feed stream, thus cooled to about 5° F., is continued through line 1 and combined with one portion of a hydrogen-rich recycle stream from line 36 to provide the desired hydrogen/hydrocarbon ratio, said recycle stream having a temperature of about −50° F. and originating as hereinafter described. The combined stream is then continued through line 3 to a first heat exchanger 29 wherein the temperature of the combined stream is increased to about 77° F., and then to a second heat exchanger 4 wherein the temperature is further increased to about 1081° F. In the first heat exchanger 29, the combined stream is heated by indirect heat exchange with a dried reactor effluent stream recovered from a dryer 14 and passing through line 26 at a temperature of about 89° F., and in the second heat exchanger 4, the combined stream is further heated by indirect heat exchange with a reactor effluent stream recovered through line 9 at a temperature of about 1081° F. Further heating of the combined stream is accomplished by means of a heater 5 to provide the desired reactor inlet temperature, the pressure at this stage having been reduced to about 22 psig due to pressure drop through the system.

The dehydrogenation reactor 6 preferably comprises multiple stacked reaction zones, and the combined stream is processed serially through said zones each of which contains a particulate catalyst disposed as an annular-form bed movable downwardly through said zones. The combined stream is then processed through said annular-form beds in a substantially radial flow and, since the dehydrogenation reaction is endothermic in nature, intermediate heating of the reactant stream between zones is the preferred practice. The moving catalyst bed permits a continuous addition of fresh and/or regenerated catalyst through conduit 7, and the withdrawal of spent catalyst through conduit 8. The moving bed system herein contemplated is illustrated in U.S. Pat. No. 3,647,680 in conjunction with a continuous catalyst regeneration system, and in U.S. Pat. No. 3,978,150 with reference to the dehydrogenation of paraffinic hydrocarbons.

In any case, the hot effluent stream from the dehydrogenation reactor 6 is recovered through line 9 and the previously mentioned heat exchanger 4. The reactor effluent stream, at a temperature of about 207° F., is then combined with a first hydrogen-rich recycle stream from line 37 originating as hereinafter described. As will become apparent, the last mentioned recycle stream is utilized to independently control the amount of vapor passing through an expander 34 and hence the amount of heat transferred in a downstream heat exchanger 30. The reactor effluent stream is then transferred through line 10 to be further combined with a hydrogen-rich recycle stream from line 48. The reactor effluent stream in combination with said recycle streams is passed through line 11 and compressed and cooled to about 225 psig and 100° F. by a compressor means 12 and a cooling means 13. In practice, said pressure is more conveniently increased in stages with provision for interstage cooling to counter the heat of compression. However, in the interest of simplicity, only one compressor and cooling means is shown.

Vessels 14 and 15 are dryers, each of which contains a fixed bed of molecular sieves or other suitable desiccant. In the present example, dryer 14 is in operation while dryer 15 is undergoing regeneration. Thus, block valves 16, 17, 18 and 19 are in the open position while block valves 20, 21, 22 and 23 are in the closed position, and the reactor effluent stream from line 11 is routed through block valve 16 and line 24 to the dryer 14. The dried reactor effluent stream is then withdrawn from the dryer 14 via line 25 and open block valve 18 to be recovered in line 26 for transfer to the gas-liquid separator 27. The dried reactor effluent stream in line 26 is processed through a series of heat exchangers 28, 29 and 30 enroute to the gas-liquid separator 27. In the first mentioned heat exchanger 28, the dried reactor effluent stream in line 26 is heat exchanged with a hereinafter described liquid hydrocarbon stream passing through line 49 at a temperature of about 56° F.; and in the second mentioned heat exchanger 29, the dried stream is further heat exchanged with the heretofore described combined stream passing through line 3 at a temperature of about −50° F.; and in the last mentioned heat exchanger 30, the dried stream is still further heat exchanged with a hydrogen-rich recycle stream flowing through line 35 at a temperature of about −127° F. The cumulative affect is a dried reactor effluent stream for introduction into the gas-liquid separator 27 via line 26 at a temperature of about −50° F. and at a pressure of about 200 psig.

The hydrogen-rich vapor that forms in the gas-liquid separator 27 at said conditions of temperature and pressure is recovered by way of an overhead line 31, one portion of said hydrogen-rich vapor phase substantially equivalent to the net hydrogen product, being diverted through line 32 and processed as later described. The balance of the hydrogen-rich vapor phase is transferred through line 33 to a work-removing type of expander 34 wherein said vapor phase is reduced in pressure to about 52 psig, and in temperature to about −127° F. The vapor phase, thus chilled, is recovered through line 35 and a heat exchanger 30 in indirect heat exchange with the dried reactor effluent stream traveling through line 26 as has been described. The hydrogen-rich vapor stream is then continued through line 35 at a temperature of about −50° F. to be recycled as follows: one portion is continued through line 36 to be combined with the feed stream introduced to the process through line 1 as has been previously described, said portion being thus recycled to the reactor 6 in admixture with said feed stream via line 3; and the remaining portion is diverted through line 37 and recycled to the gas-liquid separator 27 through the dryer 14 to serve as a refrigerant in the manner heretofore described.

That portion of the hydrogen-rich vapor phase recovered overhead from the gas-liquid separator 27 and diverted through line 32 as net hydrogen, is discharged from the process by way of line 32 in admixture with a hydrogen-rich vapor stream from line 44. This last mentioned hydrogen-rich vapor stream results from regeneration of the desiccant contained in the dryer 15. In the regeneration process, a portion of the net hydrogen is diverted from line 32 into line 38, heated in a heater 39, and then circulated over the desiccant. The hydrogen stream enters the dryer 15 by way of line 38, an open block valve 17 and line 40. The water-containing hydrogen stream, recovered by way of line 41, an open block valve 19 and line 42, enters a knock-out pot 43 wherein water is allowed to settle out for discharge through line 45. The hydrogen recovered through line 44 is then recombined with the net hydrogen in line 32 and discharged.

The liquid hydrocarbon phase that settles out in the gas-liquid separator 27 is recovered through line 46, reduced in pressure to about 25 psig, and introduced into a flash drum 47 at a temperature which is substantially the same as that of the separator 27. Residual hydrogen is flashed from the liquid hydrocarbon phase and recovered in an overhead line 48 to be combined with the reaction zone effluent stream in line 10 for eventual recycle to the gas-liquid separator 27. The liquid phase recovered from the bottom of the flash drum 47 is increased in pressure to about 446 psig and passed through line 49 and the previously mentioned heat exchanger 2 at a temperature of about −50° F. in indirect heat exchange relationship with the hydrocarbon feed stream flowing through line 1. The liquid phase stream, at a temperature of about 56° F., is then continued through line 49 to an earlier mentioned heat exchanger 28 wherein said stream is increased in temperature to about 89° F. by indirect heat exchange with the dried reactor effluent stream in line 26. The liquid phase stream is further increased in temperature by means of a heat exchanger 50 wherein said stream is passed in indirect heat exchange relationship with a hydrocarbon product stream recovered from the bottom of a depropanizer column 51. The liquid phase stream thus enters the depropanizer column via line 49 at a temperature of about 193° F. and at a pressure of about 391 psig, the depropanizer column being operated at a bottom temperature of about 237° F. at a pressure of about 371 psig, and at a top temperature of about 145° F. at a pressure of about 366 psig.

An overhead stream comprising predominantly $C_3$ and lighter hydrocarbons is discharged from the depropanizer column 51 by way of an overhead line 52. The product stream is recovered through line 53 and heat exchanged with the liquid phase stream in line 49 as aforesaid. This product stream, comprising the isobutylene product as well as unreacted isobutane, is suitably utilized in the manufacture of methyl-t-butylether wherein methanol selectively reacts with the isobutylene, or in the manufacture of t-butyl alcohol, or high octane gasoline blending alkylate, or polyisobutylene.

The following data illustrates the composition of certain relevant streams which comprise the process of the above example representing one preferred embodiment of this invention.

As heretofore stated, equilibrium reaction conditions relating to the dehydrogenation of $C_3$–$C_4$ paraffinic hydrocarbons to produce the corresponding monoolefins, as herein contemplated, generally limit the conversion to from about 30 to about 60 mol.% at optimum conditions of temperature and pressure. It follows that the overall conversion will be reduced in proportion to the amount of olefinic product recycled to the dehydrogenation zone. It is therefore essential that the hydrogen recycled to the dehydrogenation zone be substantially free of olefinic hydrocarbons. In the practice of the present invention, a substantial improvement in the separation of hydrogen from the total reaction zone effluent, comprising normally gaseous olefinic as well as paraffinic hydrocarbons, is effected whereby the recycle hydrogen is substantially free of olefinic hydrocarbons to maximize the $C_3$–$C_4$ paraffinic hydrocarbon conversion in the dehydrogenation zone in accordance with the aforesaid equilibrium reaction conditions.

| Component, lb-mols/hr | Line No. | | | | | | | | |
|---|---|---|---|---|---|---|---|---|---|
| | 1 | 3 | 9 | 32 | 36 | 48 | 49 | 52 | 53 |
| hydrogen | 0.00 | 5049.99 | 5756.25 | 703.57 | 5049.99 | 16.12 | 2.69 | 2.69 | 0.00 |
| methane | 0.00 | 234.74 | 285.70 | 32.70 | 234.74 | 4.06 | 18.26 | 18.26 | 0.00 |
| ethane | 0.00 | 8.73 | 18.81 | 1.22 | 8.73 | 0.18 | 8.86 | 8.86 | 0.00 |
| propene | 0.00 | 3.95 | 25.56 | 0.55 | 3.95 | 0.08 | 21.06 | 20.94 | 0.12 |
| propane | 6.67 | 8.82 | 16.74 | 0.30 | 2.15 | 0.04 | 14.29 | 13.69 | 0.60 |
| isobutene | 0.00 | 21.12 | 660.49 | 2.94 | 21.12 | 0.42 | 636.43 | 0.23 | 636.20 |
| 1-butene | 0.00 | 0.92 | 31.69 | 0.13 | 0.92 | 0.02 | 30.64 | 0.01 | 30.63 |
| 2-butene | 0.00 | 1.08 | 58.23 | 0.15 | 1.08 | 0.02 | 57.00 | 0.00 | 57.00 |
| butadiene | 0.00 | 0.12 | 4.20 | 0.02 | 0.12 | 0.00 | 4.06 | 0.00 | 4.06 |
| isobutane | 2283.05 | 2345.73 | 1546.46 | 8.73 | 62.68 | 1.25 | 1475.05 | 1.38 | 1473.67 |
| n-butane | 112.37 | 116.07 | 144.05 | 0.51 | 3.70 | 0.07 | 139.83 | 0.01 | 139.82 |
| Total | 2402.09 | 7791.24 | 8548.14 | 750.82 | 5389.15 | 22.28 | 2408.17 | 66.07 | 2342.10 |
| lbs/hr | 139,516 | 159,147 | 159,147 | 2735.04 | 19631.2 | 211.64 | 136,781 | 2143.8 | 134,637 |
| mol. wt. | 58.08 | 20.43 | 18.62 | 3.64 | 3.64 | 9.50 | 56.80 | 32.45 | 57.49 |
| b.p.s.d. | 16956.1 | 0 | 0 | 0 | 0 | 0 | 16359.9 | 0 | 16027.3 |
| $10^6$ s.c.f.d. | 0.0 | 70.96 | 77.86 | 6.84 | 49.08 | 0.20 | 0.0 | 0.60 | 0.0 |

We claim as our invention:

1. A catalytic dehydrogenation process which comprises the steps of:

(a) charging a $C_2$–$C_6$ paraffinic hydrocarbon into a reaction zone in admixture with hydrogen and contacting said mixture therein with a dehydrogenation catalyst at dehydrogenation conditions of temperature and pressure effecting the formation of a reaction zone effluent stream comprising hydrogen, an olefinic hydrocarbon product, and unreacted paraffinic hydrocarbon;

(b) compressing and cooling said effluent stream to a pressure and temperature effecting the formation of a liquid phase comprising said hydrocarbons and a hydrogen-rich vapor phase, and introducing said effluent stream into a gas-liquid separation zone maintained at said conditions of temperature and pressure;

(c) recovering said hydrocarbon phase;

(d) recovering one portion of said vapor phase substantially equivalent to the net hydrogen make;

(e) expanding the remaining portion of said vapor phase and effecting a substantial reduction in the pressure and temperature thereof;

(f) passing the thus cooled vapor phase in indirect heat exchange relationship with the effluent stream of step (b) to promote said temperature conditions in said gas-liquid separation zone;

(g) thereafter combining one portion of the vapor phase with the effluent stream from step (a) whereby said vapor phase is recycled to said gas-liquid separation zone to control the amount of vapor expanded in accordance with step (e) and the temperature of said separation zone in accordance with step (f); and, (h) recycling the remaining portion of the hydrogen-rich vapor phase to said reaction zone in admixture with the paraffinic hydrocarbon charged thereto in accordance with step (a).

2. The process of claim 1 further characterized in that said paraffinic hydrocarbon comprises $C_3$–$C_4$ paraffinic hydrocarbons.

3. The process of claim 1 further characterized in that said paraffinic hydrocarbon comprises isobutane.

4. The process of claim 1 further characterized with respect to step (a) in that said dehydrogenation conditions include a temperature of from about 900° to about 1400° F. and a pressure of from about 0 to about 35 psig.

5. The process of claim 1 further characterized with respect to step (b) in that said effluent stream is compressed to a pressure of from about 100 to about 400 psig and cooled to a temperature of from about −30° to about −120° F.

6. The process of claim 1 further characterized with respect to step (b) in that said effluent stream is compressed to a pressure of from about 150 to about 250 psig and cooled to a temperature of from about −30° to about −70° F.

7. The process of claim 1 further characterized with respect to step (e) in that said vapor phase is expanded to reduce the pressure thereof to from about 15 to about 75 psig, and the temperature thereof to from about −115° to about −200° F.

8. The process of claim 1 further characterized with respect to step (e) in that said vapor phase is expanded to reduce the pressure thereof to from about 40 to about 60 psig, and the temperature to from about −120° to about −130° F.

* * * * *